US009538962B1

(12) United States Patent
Hannaford et al.

(10) Patent No.: US 9,538,962 B1
(45) Date of Patent: Jan. 10, 2017

(54) HEADS-UP DISPLAYS FOR AUGMENTED REALITY NETWORK IN A MEDICAL ENVIRONMENT

(71) Applicant: Verily Life Sciences LLC, Mountain View, CA (US)

(72) Inventors: Blake Hannaford, Seattle, WA (US); Joëlle Karine Barral, Mountain View, CA (US); Eden Rephaeli, Menlo Park, CA (US); Christine Denise Ching, Mountain View, CA (US); Vikram Singh Bajaj, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 122 days.

(21) Appl. No.: 14/587,560

(22) Filed: Dec. 31, 2014

(51) Int. Cl.
*A61B 5/00* (2006.01)
*G06F 3/14* (2006.01)
*G02B 27/01* (2006.01)

(52) U.S. Cl.
CPC ........... *A61B 5/7445* (2013.01); *G02B 27/017* (2013.01); *G06F 3/1423* (2013.01)

(58) Field of Classification Search
CPC ..... A61B 5/7445; A61B 5/743; G02B 27/017; G06F 3/011; G06F 3/1423
See application file for complete search history.

(56) References Cited

U.S. PATENT DOCUMENTS

2014/0081659 A1* 3/2014 Nawana ................. A61B 34/20 705/3
2014/0247926 A1* 9/2014 Gainsboro .......... H04M 3/2281 379/88.01

OTHER PUBLICATIONS

Williams et al., "Surgeon Information Transfer and Communication Factors Affecting Quality and Efficiency of Inpatient Care", Annals of Surgery, 2007, 245(2), 159-169.
(Continued)

*Primary Examiner* — Larry Sternbane
(74) *Attorney, Agent, or Firm* — McDonnell, Boehnen, Hulbert & Berghoff LLP

(57) ABSTRACT

A system for providing networked communications includes a plurality of head-mountable devices, each in communication with a control system via a communication network. Each of the plurality of head-mountable devices includes a display, and may also include an image-capture device and/or a microphone. The control system receives, via the communication network, surgical data of a patient obtained from at least one source of surgical data. Wearers of the head-mountable devices may select aspects of the surgical data and the control system causes those selected aspects to be displayed on the respective wearable device. The control system may also generate alerts and cause the alerts to be displayed on the wearable devices. An alert may include a notification that additional surgical data is available for access by the wearer of the head-mountable device.

27 Claims, 13 Drawing Sheets

(56) References Cited

OTHER PUBLICATIONS

Kohn et al., "To Err is Human: Building a Safer Health System", National Academy of Sciences, 2000, http://www.nap.edu/catalog/9728.html, 312 pages.
Committe Opinion, "Patient Safety in the Surgical Environment", The American College of Obstetrics and Gynecologists, 2010, No. 464, 5 pages.
Gawande, A., "Atul Gawande's 'Checklist' for Surgery Success", 2010, NPR Books, 18 pages.
Way et al., "Effect of Noise on Auditory Processing in the Operating Room", J. Am. Coll. Surg., 2013, 933-938.
Navab et al., "First Deployments of Augmented Reality in Operating Rooms", IEEE Computer Society, 2012, 48-55.

\* cited by examiner

HEADS-UP DISPLAYS FOR AUGMENTED REALITY NETWORK IN A MEDICAL ENVIRONMENT

BACKGROUND

Unless otherwise indicated herein, the materials described in this section are not prior art to the claims in this application and are not admitted to be prior art by inclusion in this section.

A surgical team may comprise a number of medical professionals, each playing an assigned role and each managing various aspects of surgical data captured during, or even before, a surgical procedure. This surgical data may include surgical images and video, surgical instrument parameters, patient health parameters (e.g., vital signs), lab results, etc. A variety of technologies exists to extract this data from the surgical setting and save it in a medical records database, or elsewhere for later analysis. However, during a surgical procedure, these various aspects of surgical data often remain under the control of the surgical team member that captured or generated the data and may not be readily and immediately available to others on the team. For example, in a surgical robotics scenario, such as a laparoscopic surgery, only the surgeon may have an optical visual interface to the surgical field. Further, some members of the surgical team, such as a patient's general practitioner or a radiologist, may not be located within the operating room during a surgical procedure, but may benefit from being aware of the status of the surgery and/or being in communication with those within the operating room.

Open communication and data sharing among surgical team members can play an important role in reducing medical errors in the operating room. In some cases, however, team communication can be impeded by user interface technologies. For example, surgical robotics consoles tend to be immersive for the surgeon, which can encumber team communication and performance among the operating room team. At the same time, it can be important for a surgical team member to remain visually focused on the surgical site.

SUMMARY

Some embodiments of the present disclosure provide a method including: (i) receiving, by a control system, surgical data of a patient obtained from at least one source of surgical data, wherein the control system is in communication with a plurality of head-mountable devices via a communication network, and wherein each of the plurality of head-mountable devices comprises a display; (ii) receiving, by the control system from a first of the plurality of head-mountable devices, via the communication network, a selection by a wearer of the first of the plurality of head-mountable devices of at least one aspect of the surgical data; (iii) transmitting to the first of the plurality of head-mountable devices via the communication network, at least one instruction configured to cause the display of the first of the plurality of head-mountable devices to display the at least one aspect of surgical data; (iv) generating, by the control system, at least one alert; and (v) transmitting to the first of the plurality of head-mountable devices via the communication network, at least one instruction configured to cause the display of the first of the plurality of head-mountable devices to display the alert.

Some embodiments of the present disclosure provide a system including: (i) receiving, by a first of a plurality of head-mountable devices, an instruction by a wearer of the first of the plurality of head-mountable devices to select at least one aspect of surgical data of a patient obtained from at least one source of surgical data, wherein each of the plurality of head-mountable devices includes a display; (ii) displaying the selected at least one aspect of surgical data on the display of the first of the plurality of head-mountable devices; (iii) receiving, by the first of the plurality of head-mountable devices, an alert that additional surgical data is available for access by the first of the plurality of head-mountable devices; (iv) displaying the alert on the display of the first of the plurality of head-mountable devices; (v) receiving, by the first of the plurality of head-mountable devices, an instruction by the wearer of the first of the plurality of head-mountable devices to select the additional surgical data available for access; and (vi) displaying the additional surgical data on the display of the first of the plurality of head-mountable devices.

Some embodiments of the present disclosure provide a method including: (i) a plurality of head-mountable devices, each of the plurality of head-mountable devices comprising a display; and (ii) a control system in communication with each of the plurality of head-mountable devices via a communication network, the control system comprising: (a) a processor; (b) a computer-readable medium; and (c) program instructions stored in the computer readable medium, wherein the program instructions are executable by the processor to cause the control system to perform functions comprising: (1) receiving, via the communication network, surgical data of a patient obtained from at least one source of surgical data; (2) receiving from a first of the plurality of head-mountable devices, via the communication network, a selection of at least one aspect of the surgical data made by a wearer of the first of the plurality of head-mountable devices; (3) transmitting to the first of the plurality of head-mountable devices via the communication network, at least one instruction configured to cause the display of the first of the plurality of head-mountable devices to display the at least one aspect of surgical data; (4) generating at least one alert; and (5) transmitting to the first of the plurality of head-mountable devices via the communication network, at least one instruction configured to cause the display of the first of the plurality of head-mountable devices to display the alert.

These as well as other aspects, advantages, and alternatives, will become apparent to those of ordinary skill in the art by reading the following detailed description, with reference where appropriate to the accompanying drawings.

DETAILED DESCRIPTION

Figure 1:
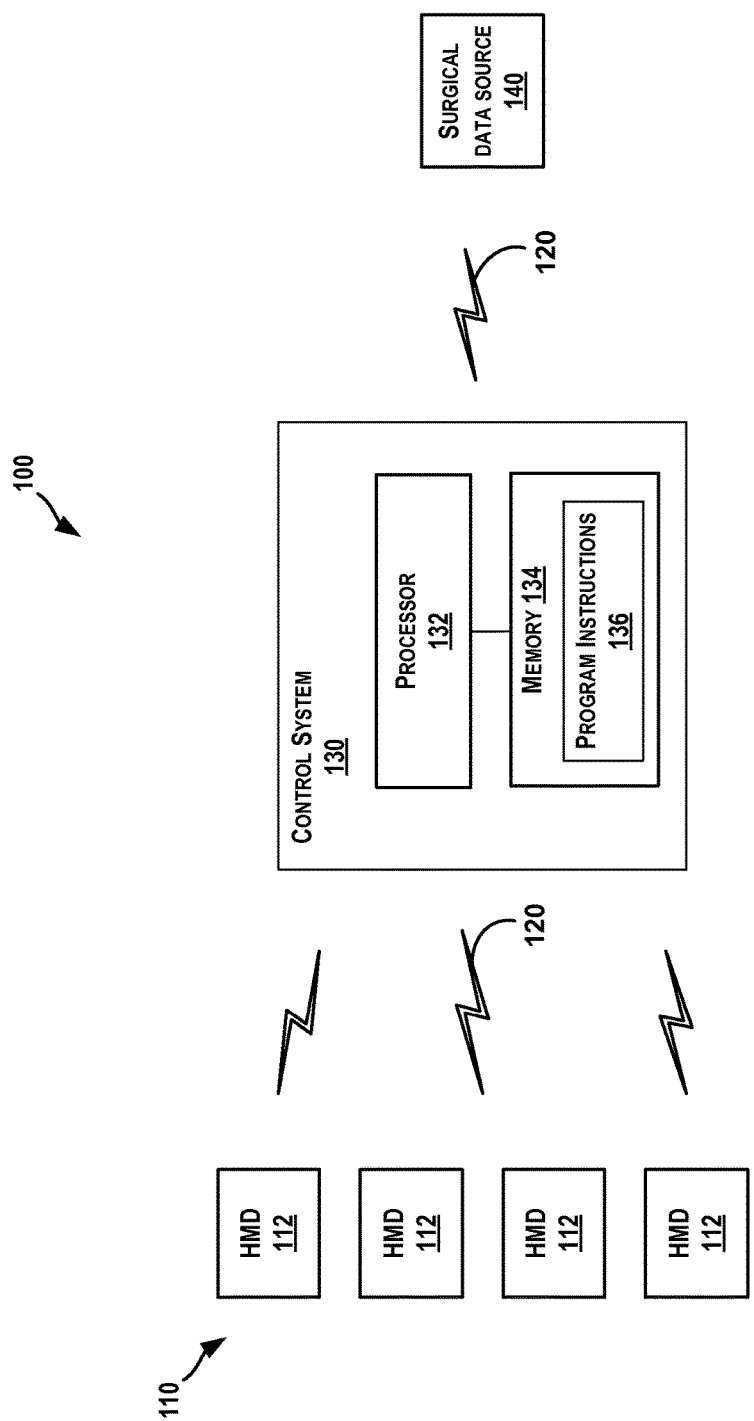
FIG. 1 is a functional block diagram of an example system, including a plurality of networked head-mountable devices.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

A system for providing networked communications between members of a surgical team can include a plurality of wearable computing devices. Each member of a surgical team may wear one of the computing devices, which are each linked via a communication network. Wearable computing devices with near-eye displays may also be referred to as "head-mountable displays" (HMDs), "head-mounted displays," "head-mounted devices," or "head-mountable devices." A head-mountable display places a graphic display or displays, such as a heads-up display, close to one or both eyes of a wearer. To generate the images on a display, a computer processing system may be used. Such displays may occupy a wearer's entire field of view, or occupy only a portion of a wearer's field of view. Further, head-mounted displays may vary in size, taking a smaller form such as a glasses-style display or a larger form such as a helmet, for example.

The use of head-mountable or other wearable devices in the operating room may provide several advantages. As the hands of operating room team members are generally busy a computing device worn on or close to the body and that is capable of displaying useful information in the field of view of the team member may be advantageous, especially where the device recognizes voice, eye gaze, gestures or other non-tactile commands. Operating room team members' hands must also remain sterile during a surgical procedure. Wearable computing technology that incorporates voice or other non-tactile command recognition expands the actions available to the surgical team without leaving the sterile field (phone calls, music tuning, etc.).

Further, a head-mountable device with a heads-up display may provide operating room team members with multiple vantage points of the surgical field. For instance, it may be useful for a surgeon to have a zoomed-in field of view for visual feedback of fine surgical movements, and also a zoomed-out movement providing orientation with respect to the patient's body. Advanced visualization modalities, such as fluorescent or hyperspectral imaging, may be projected onto the heads-up display, providing a team member with additional layers of information. Preoperative and anatomical images may also be superimposed onto real-time surgical images and projected onto the heads-up display. A heads-up display may also allow a surgical team member to perform some fatiguing and awkward surgical tasks in a more ergonomic fashion or position.

Each operating room member may need to consult various sources of electronic information, including patient vital signs, preoperative images, medical records, etc. A wearable device with a heads-up display may also allow a surgical team member to take advantage of these additional aspects of surgical information, while remaining visually focused on the surgical site. Wearable technology may also be configured to capture and record surgical data, including video, vital signs, drug administration, or an action item, e.g., the introduction of a new instrument in the sterile field.

The networking capabilities of head-mountable computing devices may also facilitate intra-team communication, which may facilitate coordinated actions and provide for a safer surgical environment, especially where the attention of one or more team members is impeded by other user interface technologies, such as surgical robotic consoles. In one aspect, a network of head-mountable devices may allow surgical team members to share or direct specific information to the attention of another team member. This may be particularly useful where an aspect of the surgical data being generated or captured during a surgical procedure is under the direct control or management of a single team member. For example, a networked head-mountable device may provide a means for communication of robot state information beyond the surgeon, who is in direct control, and to the entire surgical team.

Networked user interfaces may also streamline workflow automation in the operating room. For example, completion of checklists, which have been recognized as a way to reduce errors in the operating room, can also be facilitated by the use of head-mountable displays. Each team member may simultaneously view the checklist questions, provide their responses, and view responses by the entire team. Similarly, pre- and postoperative counting and documentation of surgical objects (e.g. tools/sponges) can be shared and coordinated among the entire surgical team, especially where visualization of the surgical site is made available to and projected on the heads-up display of each team member. The preoperative exchange of names (introductions) among the surgical team has also been shown to reduce complications by 35%. See, e.g., Atul Gawande's 'Checklist' For Surgery Success (available at http://www.npr.org/templates/story/story.php?storyId=122226184). By, for example, introducing team members by their first names, team members may feel more comfortable suggesting corrections or noting errors, even amongst members of varying seniority and educational and hierarchical levels. This may be facilitated by superimposing the names of each team member on the heads-up display of a networked wearable computing device. In addition, networked interfaces may also prevent "wrong-site surgery" incidents where the system may be configured to accept and cross-check independent designations of the intended surgery site by each team member. The networked system may also be linked to an electronic medical record or other health-care management software.

The head-mountable devices provided to each member of the surgical team may execute a software interface having at least three functions: information retrieval, verbal and/or nonverbal communication, and augmented reality, as well as the ability to capture data from these functions. Each team member will be able to view an interface customized for their role in the surgical procedure and, in some cases, their physical location in the operating room. As an example, the surgeon might benefit from one or more video images of the surgical theater (small field-of-view, large field-of-view) or images from different perspectives, including those from the perspective of other team members. Further, the type of surgery may dictate some features of the data displayed on the heads-up display. Team members may also customize or reconfigure the graphical user interface of their respective devices.

As part of the information retrieval function, team members can select from surgical data sources specific to the patient and procedure. Selected data may be displayed in an effective manner with a navigation interface. Further, as part of the verbal and nonverbal communication function, a team member can bring retrieved information to the attention of another team member. Using, for example, verbal commands or gestures, a team member can select other team members or a group with an easy gesture and share or make available certain surgical data with those selected team members. The selected team members may receive a notification that the data has been shared with them. Data captured during a surgical procedure may also be shared, in real time, with others outside of the surgical team and, vice versa. For example, a surgeon may send real-time surgical images captured during a procedure to the patient's oncologist. The oncologist may review the images and send a notification to the surgeon when her report is available for review. The notification may be projected on the surgeon's heads-up display, allowing the surgeon to choose if and/or when she views the report. Team members may also use the wearable devices to communicate the status of the surgery to others outside of the surgical room, including the patient's family, nursing staff, or scheduling systems.

The head-mountable devices may be equipped with one or more image capture devices and/or microphones, such as bidirectional audio links Microphones may be configured to detect acoustic direct verbal communication and intelligently gate between acoustic and network-mediated speech. For example, the system may distinguish when team members are directly communicating with one another and when a team member is attempting to interface with the application. Further, the system may be equipped with speech recognition technology configured to detect nonmedical conversation such as sports team or celebrity names (which may serve as a potential distraction) and the surgical team could be alerted to refocus on the operation. The system may also be used to detect, alert and refocus the surgical team in critical situations, such as a code blue event.

Further, video and still image data may be gathered from cameras within the operating room, cameras deployed in the surgical site (e.g., as part of an endoscope or laparoscopic device), and/or image-capture devices on one or more head-mountable devices. Team members may select image data collected from one or more of these sources to be projected on their respective heads-up displays. In addition, video captured from an image-capture device on the head-mountable device of one team member, and therefore captured from the point of view of that team member, can be made available to and viewed by others on the team. In addition, a team member may select preoperative images of the patient, for example, video data saved to the cloud or even relevant image data of another patient.

Other data, in addition to image data, may also be retrieved by the networked head-mountable devices. For example, the devices may access the Internet or other electronic sources to retrieve relevant medical references, such as an anatomical atlas or other textbook, or other health-related data, such as information from the CDC or NIH. Surgical team members may also access and view a patient's electronic medical records from the head-mountable device.

Communications and image data captured by the head-mountable devices may also be recorded (or translated and sent to the cloud), in some cases automatically, for quality, insurance and/or other purposes. For example, video and sound recordings of a surgical procedure may be used for training purposes. The pre-collected data may be recalled and projected onto a head-mountable display to revisit and study the procedure as perceived from each individual team member. Alternatively, nurses, surgeons or other medical professionals in training may "participate" in surgical procedures in real time using networked head-mountable devices. Further, some members of the surgical team may be outside of the operating room and may use a networked head-mountable device to remotely monitor or guide the surgical procedure.

In another aspect, as part of the augmented reality feature of the application, the system may be configured to generate 2D or 4D imagery of the surgical field from the distinct perspective of each user, thereby allowing all team members to view the surgical field. Such images can be transformed by such means as rotation and translation based on the wearer's position relative to the patient's body. These images may be projected onto each team member's heads-up display and superimposed over the respective field of view of that team member. Such imagery could include the patient's internal organs (as captured for example by a laparoscope) and also the position and angulation of surgical instruments, and also a computer graphics model of the surgical instruments, which would move as the actual instruments move. Laparoscopic or other video image data captured during the procedure may be used to generate these images. Further, the system may detect each individual team member's location within the operating room (e.g., based on the location of their respective head-mountable devices) in order to generate the perspective imagery. The resulting display would allow all team members to observe the surgery site and instruments in real time and from their own perspective. This may be useful for avoiding unwanted interactions between surgical instruments where more than one team member is simultaneously operating instruments within the surgical site, such as where a surgeon is operating a surgical robot from a remote robotics console and a surgical assistant is using a laparoscopic instrument.

In addition, the networked head-mountable devices may be capable of implementing a sterile cockpit in the operating room by allowing surgical team members to interface with and control other instruments, devices and electronic systems. For example, the head-mountable devices may enable a team member to control lighting or a music system within the operating room with a verbal or other command. The head-mountable devices may also be configured to capture images from a C-arm fluoroscope during a fluoroscopically guided procedure in response to a verbal or other command of the surgeon.

Other configurations, modes and methods of operation, and other embodiments are anticipated. While examples using head-mountable devices are described, the systems and/or methods described herein could be implemented with other wearable computing devices. Further, systems and methods as described herein could be used in environments other than surgical environments (e.g., construction sites, industrial fabrication environments, scientific research sites, etc.) where networked communications and data sharing may be desirable. Other applications and configurations of systems as described herein are anticipated.

It should be understood that the above embodiments, and other embodiments described herein, are provided for explanatory purposes, and are not intended to be limiting.

II. EXAMPLE SURGICAL COMMUNICATION SYSTEM

FIG. 1 is a simplified block diagram illustrating the components of networked surgical communication system 100, according to an example embodiment. System 100 may include a plurality of wearable computing devices 110, such as head-mountable devices (HMDs) 112. Each of the plurality of head-mountable devices comprises a display (see FIGS. 4A-4G). The system 100 also includes a control system 130 in communication with each of the plurality of HMDs 112 via a communication network 120. The control system 130 may also be in communication with one or more sources of surgical data 140. Further, while the control system 130 is depicted in FIG. 1 and described herein as being a separate entity from the HMDs 112, it is contemplated that the functions performed by the control system 130 may be performed by each HMD 112.

The wearable devices 110 and sources of surgical data 140 may be configured to transmit data via one or more communication interfaces over one or more communication networks 120 to the control system 130. The one or more communication interfaces may include any means for the transfer of data, including both wired and wireless communications. In one embodiment, the communication interface includes a wireless transceiver for sending and receiving communications to and from the control system 130. The wearable devices 110 may also be configured to communicate with one another via any communication means.

The communication network 120 may take a variety of forms, including for example, a cellular telephone network, a land-line telephone network, a packet-switched network such as the Internet, and/or a combination of such networks. Other examples are possible as well. The communication network 120 may be configured for performing various operations, including for example, facilitating communication between the wearable device(s) 110, sources of surgical data 140, and control system 130, using one or more protocols. For illustrative purposes, the communication network 120 is depicted in FIG. 1 as a single communication network through which the wearable device(s) 110, sources of surgical data 140, and control system 130 may communicate. Notably however, the communication network 120 may include two or more separate communication networks, each configured for facilitating communication between select systems or devices.

Surgical data may include any data collected during a surgical procedure, such as vital signs or surgical instrument parameters, or any patient data collected from the patient undergoing a surgical procedure, such as medical records or pre-operative images, or any other related data, including images from previous related surgeries or medical texts, etc. For example, surgical data may include surgical image data (real-time or preoperative), speech or communications, surgical instrument parameter data or patient data. The one or more sources of surgical data 140 may include image capture devices located within the operating room, on a surgical instrument, or on one or more of the HMDs 112; one or more microphones located within the operating room or provided on one or more of the HMDs 112; one or more sensors or other devices on the surgical instruments for collecting surgical parameter data (e.g., instrument position, instrument temperature, vacuum pressure, etc.); one or more sources of patient data, including sensors for detecting physiological parameter data of a patient (e.g., heart rate, respiration rate, blood pressure, body temperature, brain activity, etc.); and one or more remote sources, such as the internet, databases, including the cloud, containing, for example pre-surgical images of the patient, medical records of the patient, image data from previous procedures, etc. or other individuals or systems located outside of the operating room, including laboratories, or other departments within a medical center, etc. Accordingly, the wearable computing devices 110 themselves may also be sources of surgical data, including verbal communications between one or more wearers of the devices and image data.

The control system 130 includes a processor 132 and a memory 134. Example processor(s) 132 include, but are not limited to, CPUs, Graphics Processing Units (GPUs), digital signal processors (DSPs), application specific integrated circuits (ASICs). Memory 134 is a non-transitory computer-readable medium that can include, without limitation, magnetic disks, optical disks, organic memory, and/or any other volatile (e.g. RAM) or non-volatile (e.g. ROM) storage system readable by the processor 132. Memory 134 can store surgical data, program settings (e.g., to adjust behavior of the wearable devices 110), user inputs (e.g., communicated from a user interface on one or more of the wearable devices 110 or a remote device), etc. Memory 134 can also include program instructions 136 for execution by the processor 132 to cause the control system 130 to perform functions specified by the instructions. The functions could include any of the methods described herein.

For example, the program instructions 136 may cause the control system 130 to perform functions relating to networking communications and surgical data between and among the plurality of head-mountable devices 112. In one example, the control system 130 may receive, via the communication network 120, surgical data of a patient obtained from at least one source of surgical data 140. The surgical data and the one or more sources of surgical data 140 may include any of those described above. A wearer of at least one of the HMDs 112 may make a selection of at least one aspect of the surgical data. For example, the wearer may select certain vital signs of the patient and surgical data depicting one or more views of the surgical field. The control system 130 may receive the selection via the communication network 120 and transmit to the wearable device 112 from which the selection was received, at least one instruction configured to cause the display of the HMD to display the selected aspects of surgical data.

The program instructions 136 may cause the control system 130 to perform functions including generating one or more alerts and transmitting to one or more of the plurality of HMDs 112, via the communication network 120, at least one instruction configured to cause the display of the respective HMDs 112 to display the alert. The alert may comprise a notification that additional surgical data is available for access by an HMD 112. As described above, each wearer of an HMD 112 may choose to make certain surgical data, such as data that is largely within the control of or being managed by that wearer, available for other members of the team (also wearing HMDs). Accordingly, the alert may comprise a notification that another wearer of an HMD 112 has made additional surgical data available for access. In some examples, the additional surgical data may include any surgical data that is not already projected or displayed, or available for display, on the HMD of a particular wearer. Further, the additional surgical data may include a message generated by one of the surgical-team members, or another person outside of the operating room, directed to another team member. The alert may, therefore, comprise a notification that the wearer of the HMD 112 has received a message. This messaging function may provide a discreet way for a team member, or other individual monitoring the surgical procedure, to notify another team member that an error has been made. In addition, the alert may comprise a notification that a source of surgical data 140 has made additional surgical data available for access by an HMD. For example, the alert may indicate that a laboratory or other department may make test results available.

Figure 2:
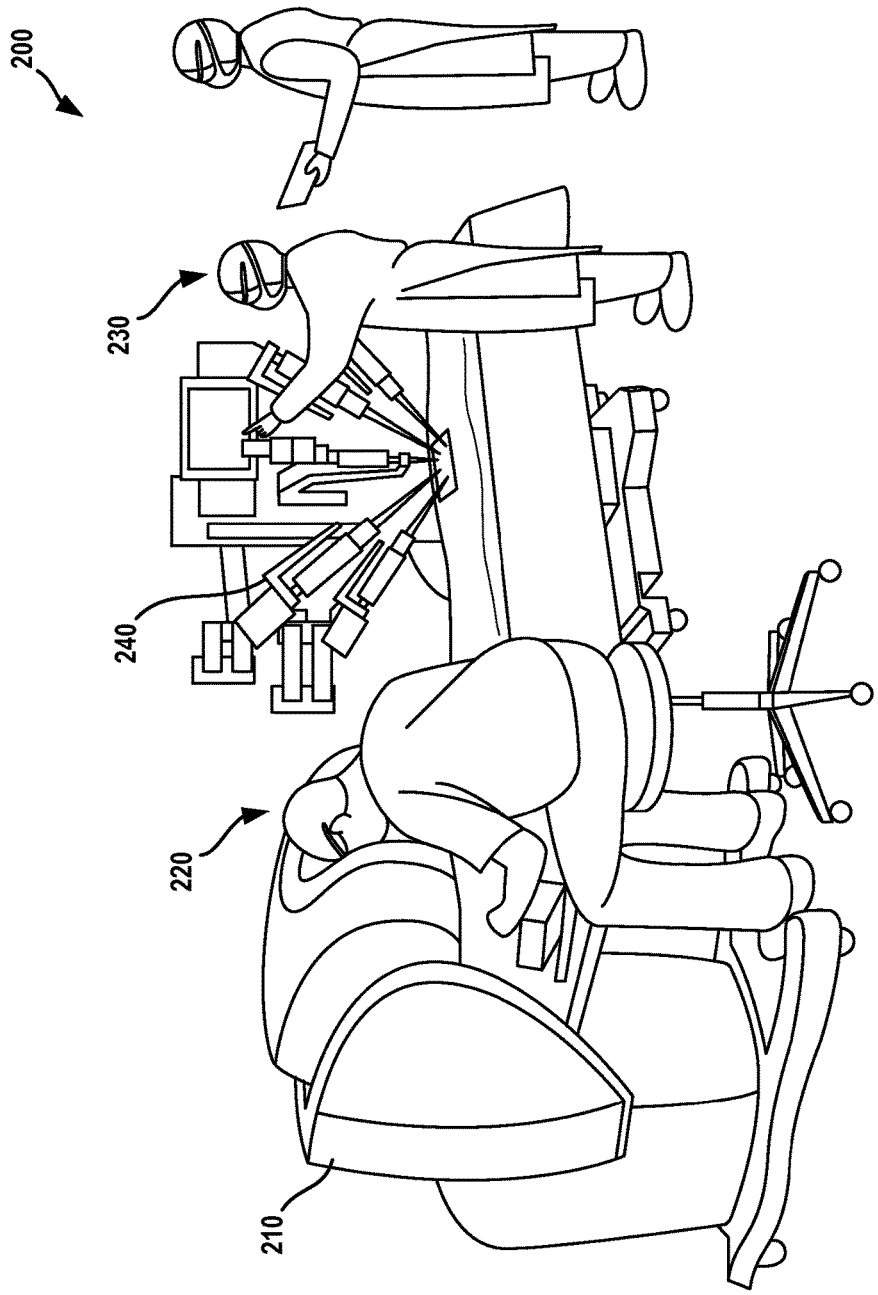
FIG. 2 illustrates an example operating room including a robotics console.

The communication system 100 implemented with one or more HMDs 112 used by the members of a surgical team may allow for easy selection and communication of information among the team members. The system 100 may ensure that a surgeon engaged in an immersive robotics console may remain aware of information readily available to other team members, and vice versa. As shown in FIG. 2, when operating at a robotics console 210, the surgeon 220 does not have an unobstructed view of the operating room 200, may not have an unobstructed audio path from others in the suite, and may be so engaged in the console that she is unable to pay attention to or perceive events occurring in the operating room. The HMD 112 may provide the surgeon 220 with other views of the operating room or surgery site, clear audio from other team members and other surgical information that may be relevant and, in some circumstances, critical to the surgery and the surgeon's tasks. In addition, the communication system 100 and associated HMDs 112 may allow the other members of the surgical team, such as an assistant 230 operating one or more surgical instruments 240 at the patient's bedside, to be aware of information under the control of the surgeon, such as position and parameter data of the robotics instruments.

Figure 3:
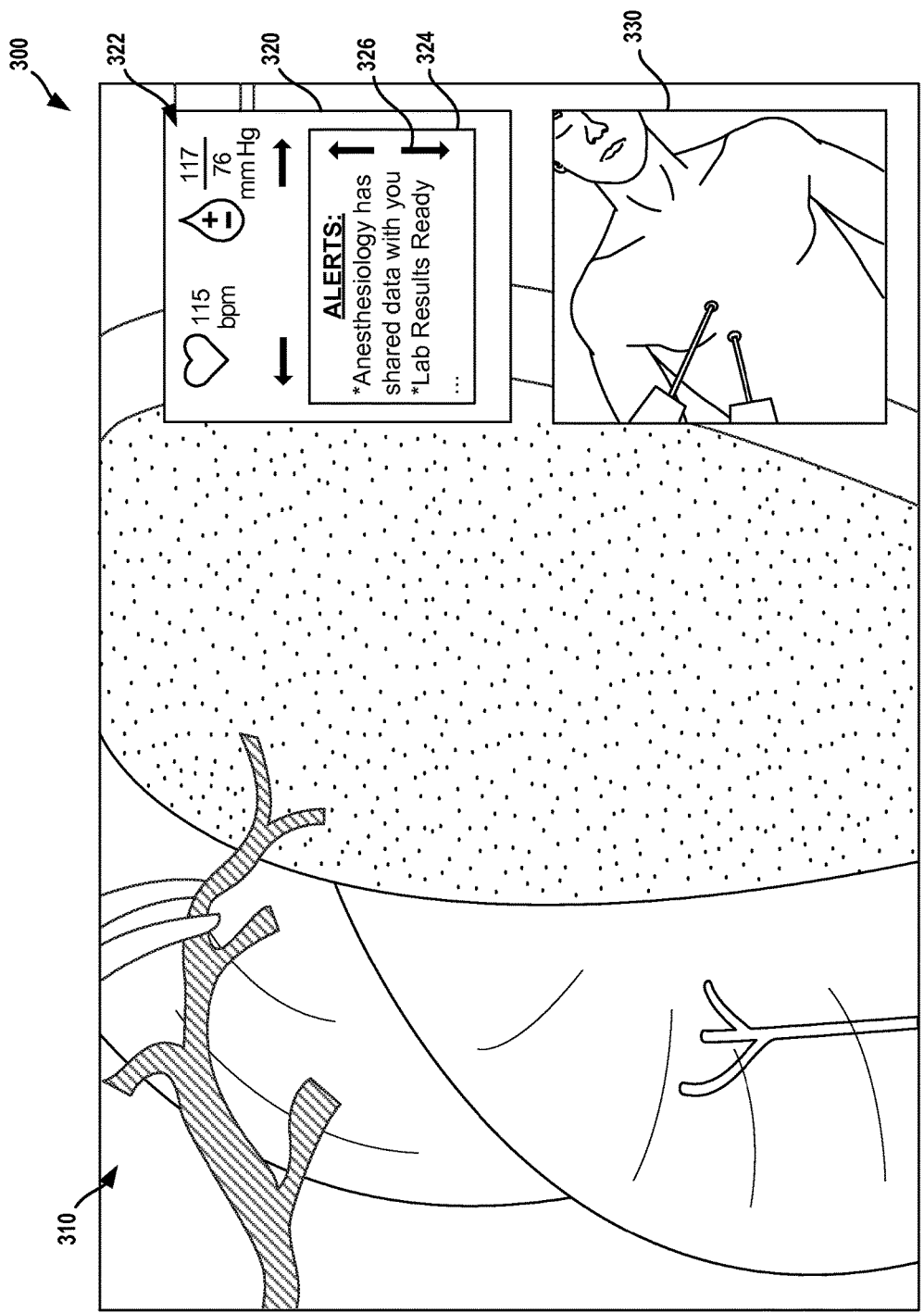
FIG. 3 illustrates an example user interface of a head-mountable device.

FIG. 3 illustrates an example user interface 300 of a head mountable device, such as HMD 112. In one example, user interface 300 may include a display 310, which may include a display or projection of surgical image data, such as image data depicting the field of view of the wearer of the HMD, the field of view of another wearer of an HMD, the field of view of a surgical instrument or other image capture device, or any other aspect of surgical data selected by the wearer of the HMD. In addition, the user interface 300 may also include a navigation pane 320 and a secondary display 330, which may be projected over the display 310. One or more aspects of surgical data 322 may be displayed within the navigation pane 320. The navigation pane 320 may also include an alerts pane 324 within which one or more alerts received by an HMD may be displayed. In addition, the navigation pane 320 may include one or more controls 326 to allow the wearer of the HMD to scroll through additional surgical data the wearer has selected or alerts that have been sent to the HMD. Further, the wearer of the HMD may indicate one or more selections of surgical data via the controls 326. The wearer of the HMD may choose to display a different view of the surgical field, captured by a different image capture device, within the secondary display 330. For example, as shown in FIG. 3, a zoomed-in image can be displayed on the main display 310 and a zoomed-out view can be displayed on the secondary display 330. Other orientations and configurations of the user interface 300 are also contemplated.

In addition to creating a record of the patient-centric data collected during a surgical procedure, the system of networked HMDs may also collect data from the surgical team members. Each of the plurality of HMDs may also include one or more sensors for collecting physiometric or performance data from the wearer of the respective device. For example, the HMD may include one or more of an accelerometer, IMU, proximity sensor, microphone, gyroscope, magnetometer, barometer, thermometer, optical/multispectral sensor, ultrasonic sensor, Doppler sensor, galvanic skin response (GSR) instrument, odometer, pedometer, a location-tracking sensor (e.g., a GPS device), and a clock. Physiometric or performance data may include such as heart rate, blood pressure, respiration rate, blood oxygen saturation ($SpO_2$), skin temperature, skin color, galvanic skin response (GSR), muscle movement, eye movement, blinking, and speech. The collected physiometric data may, in some cases, be used to determine the health state and performance level of the surgical team members. This information may dictate whether, for example, a member of the team is not operating at full health or physical or mental capacity, which could be a risk for the patient undergoing surgery.

Further, the HMD may also record other metrics of each team member, such as the number of hours a team member has been in the OR, the types of procedures performed, the time spent on each procedure, if any adverse events occurred during a procedure, and the other professionals with which the team member has worked. This data can be used to inform pricing or for training or accreditation purposes. Further, surgical team members may use the HMD to recall these metrics of fellow team members.

In situations in which the systems and methods discussed herein collect personal information about users, or may make use of personal information, the users may be provided with an opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

III. EXAMPLE WEARABLE COMPUTING DEVICES

Systems and devices in which example embodiments may be implemented will now be described in greater detail. In general, an example system may be implemented in or may take the form of a wearable computer (also referred to as a wearable computing device). In an example embodiment, a wearable computer takes the form of or includes a head-mountable device (HMD).

An HMD may generally be any display device that is capable of being worn on the head and places a display in front of one or both eyes of the wearer. An HMD may take various forms such as a helmet or eyeglasses. As such, references to "eyeglasses" or a "glasses-style" HMD should be understood to refer to an HMD that has a glasses-like frame so that it can be worn on the head. Further, example embodiments may be implemented by or in association with an HMD with a single display or with two displays, which may be referred to as a "monocular" HMD or a "binocular" HMD, respectively.

Figure 4A:
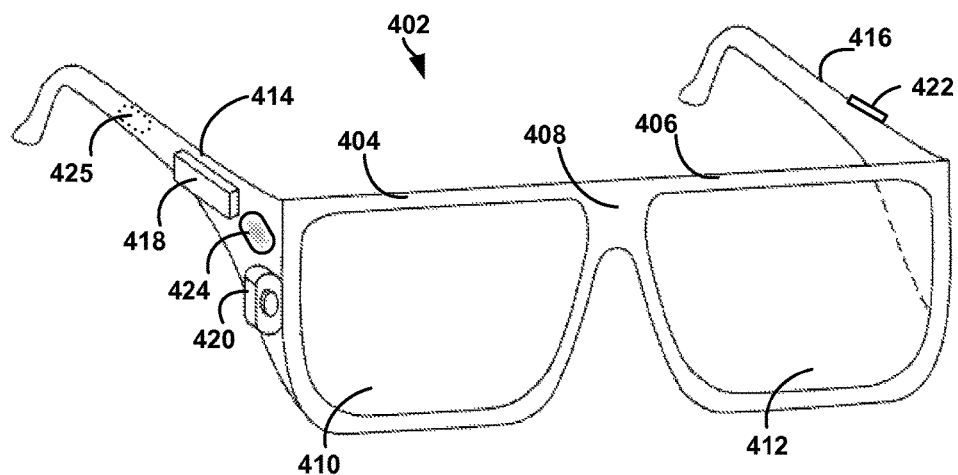
FIG. 4A illustrates a wearable computing system according to an example embodiment.

FIG. 4A illustrates a wearable computing system according to an example embodiment. In FIG. 4A, the wearable computing system takes the form of a head-mountable device (HMD) 402 (which may also be referred to as a head-mounted display). It should be understood, however, that example systems and devices may take the form of or be implemented within or in association with other types of devices, without departing from the scope of the invention. As illustrated in FIG. 4A, the HMD 402 includes frame elements including lens-frames 404, 406 and a center frame support 408, lens elements 410, 412, and extending side-arms 414, 416. The center frame support 408 and the extending side-arms 414, 416 are configured to secure the HMD 402 to a user's face via a user's nose and ears, respectively.

Each of the frame elements 404, 406, and 408 and the extending side-arms 414, 416 may be formed of a solid structure of plastic and/or metal, or may be formed of a hollow structure of similar material so as to allow wiring and component interconnects to be internally routed through the HMD 402. Other materials may be possible as well.

One or more of each of the lens elements 410, 412 may be formed of any material that can suitably display a projected image or graphic. Each of the lens elements 410, 412 may also be sufficiently transparent to allow a user to see through the lens element. Combining these two features of the lens elements may facilitate an augmented reality or heads-up display where the projected image or graphic is superimposed over a real-world view as perceived by the user through the lens elements.

The extending side-arms 414, 416 may each be projections that extend away from the lens-frames 404, 406, respectively, and may be positioned behind a user's ears to secure the HMD 402 to the user. The extending side-arms 414, 416 may further secure the HMD 402 to the user by extending around a rear portion of the user's head. Additionally or alternatively, for example, the HMD 402 may connect to or be affixed within a head-mounted helmet structure. Other configurations for an HMD are also possible.

The HMD 402 may also include an on-board computing system 418, an image capture device 420, a sensor 422, and a finger-operable touch pad 424. The on-board computing system 418 is shown to be positioned on the extending side-arm 414 of the HMD 402; however, the on-board computing system 418 may be provided on other parts of the HMD 402 or may be positioned remote from the HMD 402 (e.g., the on-board computing system 418 could be wire- or wirelessly-connected to the HMD 402). The on-board computing system 418 may include a processor and memory, for example. The on-board computing system 418 may be configured to receive and analyze data from the image capture device 420 and the finger-operable touch pad 424 (and possibly from other sensory devices, user interfaces, or both) and generate images for output by the lens elements 410 and 412.

The image capture device 420 may be, for example, a camera that is configured to capture still images and/or to capture video. In the illustrated configuration, image capture device 420 is positioned on the extending side-arm 414 of the HMD 402; however, the image capture device 420 may be provided on other parts of the HMD 402. The image capture device 420 may be configured to capture images at various resolutions or at different frame rates. Many image capture devices with a small form-factor, such as the cameras used in mobile phones or webcams, for example, may be incorporated into an example of the HMD 402.

Further, although FIG. 4A illustrates one image capture device 420, more image capture device may be used, and each may be configured to capture the same view, or to capture different views. For example, the image capture device 420 may be forward facing to capture at least a portion of the real-world view perceived by the user. This forward facing image captured by the image capture device 420 may then be used to generate an augmented reality where computer generated images appear to interact with or overlay the real-world view perceived by the user.

The sensor 422 is shown on the extending side-arm 416 of the HMD 402; however, the sensor 422 may be positioned on other parts of the HMD 402. For illustrative purposes, only one sensor 422 is shown. However, in an example embodiment, the HMD 402 may include multiple sensors. For example, an HMD 402 may include sensors 402 such as one or more gyroscopes, one or more accelerometers, one or more magnetometers, one or more light sensors, one or more infrared sensors, and/or one or more microphones. Other sensing devices may be included in addition or in the alternative to the sensors that are specifically identified herein.

The finger-operable touch pad 424 is shown on the extending side-arm 414 of the HMD 402. However, the finger-operable touch pad 424 may be positioned on other parts of the HMD 402. Also, more than one finger-operable touch pad may be present on the HMD 402. The finger-operable touch pad 424 may be used by a user to input commands. The finger-operable touch pad 424 may sense at least one of a pressure, position and/or a movement of one or more fingers via capacitive sensing, resistance sensing, or a surface acoustic wave process, among other possibilities. The finger-operable touch pad 424 may be capable of sensing movement of one or more fingers simultaneously, in addition to sensing movement in a direction parallel or planar to the pad surface, in a direction normal to the pad surface, or both, and may also be capable of sensing a level of pressure applied to the touch pad surface. In some embodiments, the finger-operable touch pad 424 may be formed of one or more translucent or transparent insulating layers and one or more translucent or transparent conducting layers. Edges of the finger-operable touch pad 424 may be formed to have a raised, indented, or roughened surface, so as to provide tactile feedback to a user when the user's finger reaches the edge, or other area, of the finger-operable touch pad 424. If more than one finger-operable touch pad is present, each finger-operable touch pad may be operated independently, and may provide a different function.

In a further aspect, HMD 402 may be configured to receive user input in various ways, in addition or in the alternative to user input received via finger-operable touch pad 424. For example, on-board computing system 418 may implement a speech-to-text process and utilize a syntax that maps certain spoken commands to certain actions. In addition, HMD 402 may include one or more microphones via which a wearer's speech may be captured. Configured as such, HMD 402 may be operable to detect spoken commands and carry out various computing functions that correspond to the spoken commands.

As another example, HMD 402 may interpret certain head-movements as user input. For example, when HMD 402 is worn, HMD 402 may use one or more gyroscopes and/or one or more accelerometers to detect head movement.

The HMD 402 may then interpret certain head-movements as being user input, such as nodding, or looking up, down, left, or right. An HMD 402 could also pan or scroll through graphics in a display according to movement. Other types of actions may also be mapped to head movement.

As yet another example, HMD 402 may interpret certain gestures (e.g., by a wearer's hand or hands) as user input. For example, HMD 402 may capture hand movements by analyzing image data from image capture device 420, and initiate actions that are defined as corresponding to certain hand movements.

As a further example, HMD 402 may interpret eye movement as user input. In particular, HMD 402 may include one or more inward-facing image capture devices and/or one or more other inward-facing sensors (not shown) that may be used to sense a user's eye movements and/or positioning. As such, certain eye movements may be mapped to certain actions. For example, certain actions may be defined as corresponding to movement of the eye in a certain direction, a blink, and/or a wink, among other possibilities.

HMD 402 also includes a speaker 425 for generating audio output. In one example, the speaker could be in the form of a bone conduction speaker, also referred to as a bone conduction transducer (BCT). Speaker 425 may be, for example, a vibration transducer or an electroacoustic transducer that produces sound in response to an electrical audio signal input. The frame of HMD 402 may be designed such that when a user wears HMD 402, the speaker 425 contacts the wearer. Alternatively, speaker 425 may be embedded within the frame of HMD 402 and positioned such that, when the HMD 402 is worn, speaker 425 vibrates a portion of the frame that contacts the wearer. In either case, HMD 402 may be configured to send an audio signal to speaker 425, so that vibration of the speaker may be directly or indirectly transferred to the bone structure of the wearer. When the vibrations travel through the bone structure to the bones in the middle ear of the wearer, the wearer can interpret the vibrations provided by BCT 425 as sounds.

Various types of bone-conduction transducers (BCTs) may be implemented, depending upon the particular implementation. Generally, any component that is arranged to vibrate the HMD 402 may be incorporated as a vibration transducer. Yet further it should be understood that an HMD 402 may include a single speaker 425 or multiple speakers. In addition, the location(s) of speaker(s) on the HMD may vary, depending upon the implementation. For example, a speaker may be located proximate to a wearer's temple (as shown), behind the wearer's ear, proximate to the wearer's nose, and/or at any other location where the speaker 425 can vibrate the wearer's bone structure.

Figure 4B:
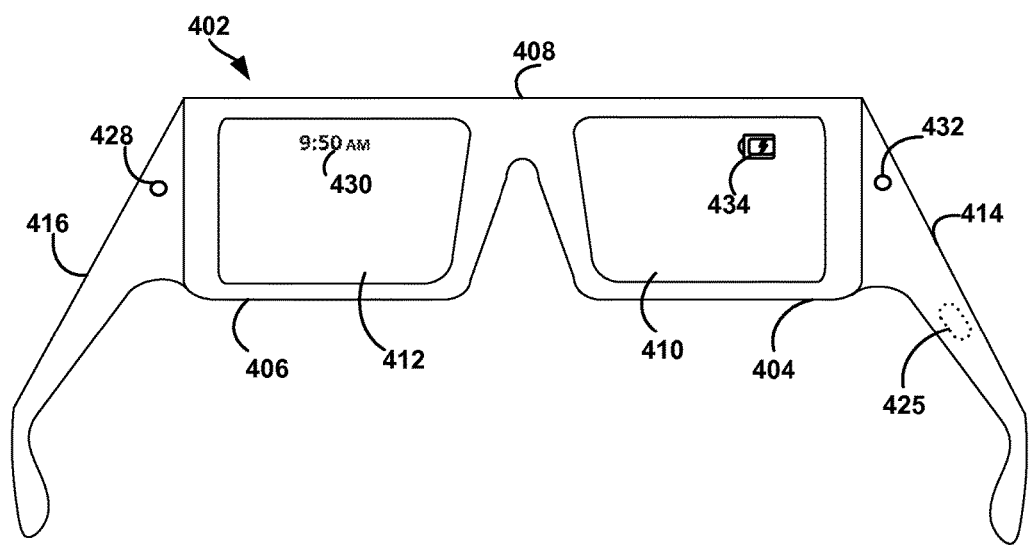
FIG. 4B illustrates an alternate view of the wearable computing device illustrated in FIG. 4A.

FIG. 4B illustrates an alternate view of the wearable computing device illustrated in FIG. 4A. As shown in FIG. 4B, the lens elements 410, 412 may act as display elements. The HMD 402 may include a first projector 428 coupled to an inside surface of the extending side-arm 416 and configured to project a display 430 onto an inside surface of the lens element 412. Additionally or alternatively, a second projector 432 may be coupled to an inside surface of the extending side-arm 414 and configured to project a display 434 onto an inside surface of the lens element 410.

The lens elements 410, 412 may act as a combiner in a light projection system and may include a coating that reflects the light projected onto them from the projectors 428, 432. In some embodiments, a reflective coating may not be used (e.g., when the projectors 428, 432 are scanning laser devices).

In alternative embodiments, other types of display elements may also be used. For example, the lens elements 410, 412 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 404, 406 for driving such a matrix display. Alternatively or additionally, a laser or LED source and scanning system could be used to draw a raster display directly onto the retina of one or more of the user's eyes. Other possibilities exist as well.

Figure 4C:
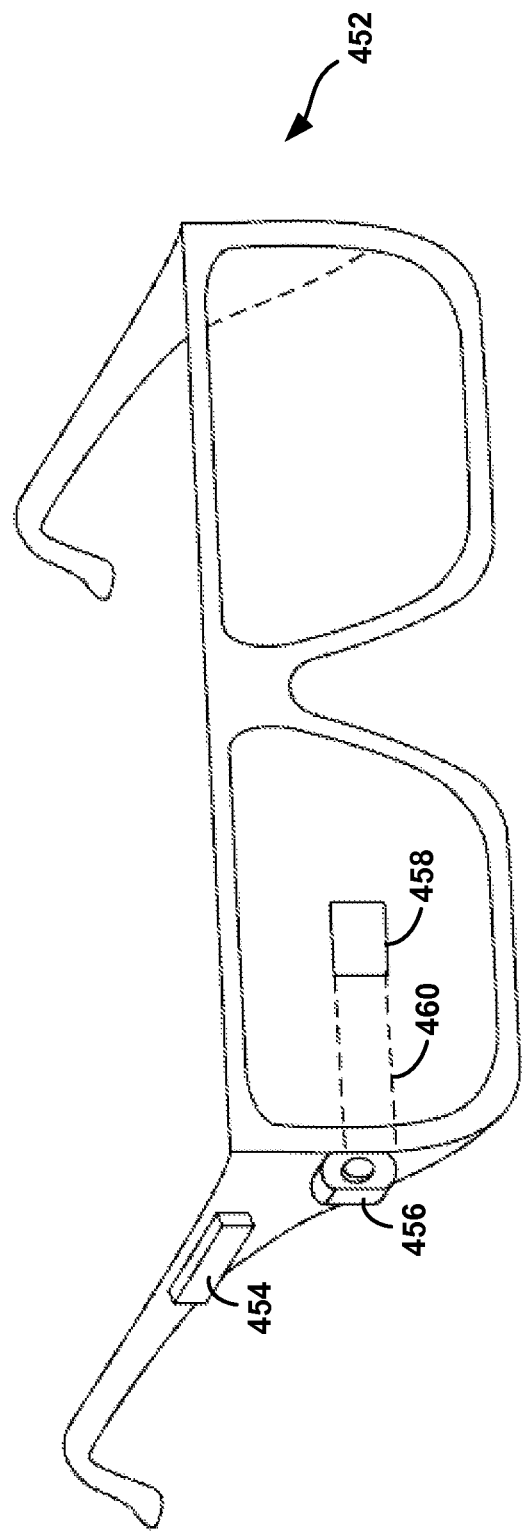
FIG. 4C illustrates another wearable computing system according to an example embodiment.

FIG. 4C illustrates another wearable computing system according to an example embodiment, which takes the form of an HMD 452. The HMD 452 may include frame elements and side-arms such as those described with respect to FIGS. 4A and 4B. The HMD 452 may additionally include an on-board computing system 454 and an image capture device 456, such as those described with respect to FIGS. 4A and 4B. The image capture device 456 is shown mounted on a frame of the HMD 452. However, the image capture device 456 may be mounted at other positions as well.

As shown in FIG. 4C, the HMD 452 may include a single display 458 which may be coupled to the device. The display 458 may be formed on one of the lens elements of the HMD 452, such as a lens element described with respect to FIGS. 4A and 4B, and may be configured to overlay computer-generated graphics in the user's view of the physical world. The display 458 is shown to be provided in a center of a lens of the HMD 452, however, the display 458 may be provided in other positions, such as for example towards either the upper or lower portions of the wearer's field of view. The display 458 is controllable via the computing system 454 that is coupled to the display 458 via an optical waveguide 460.

Figure 4D:
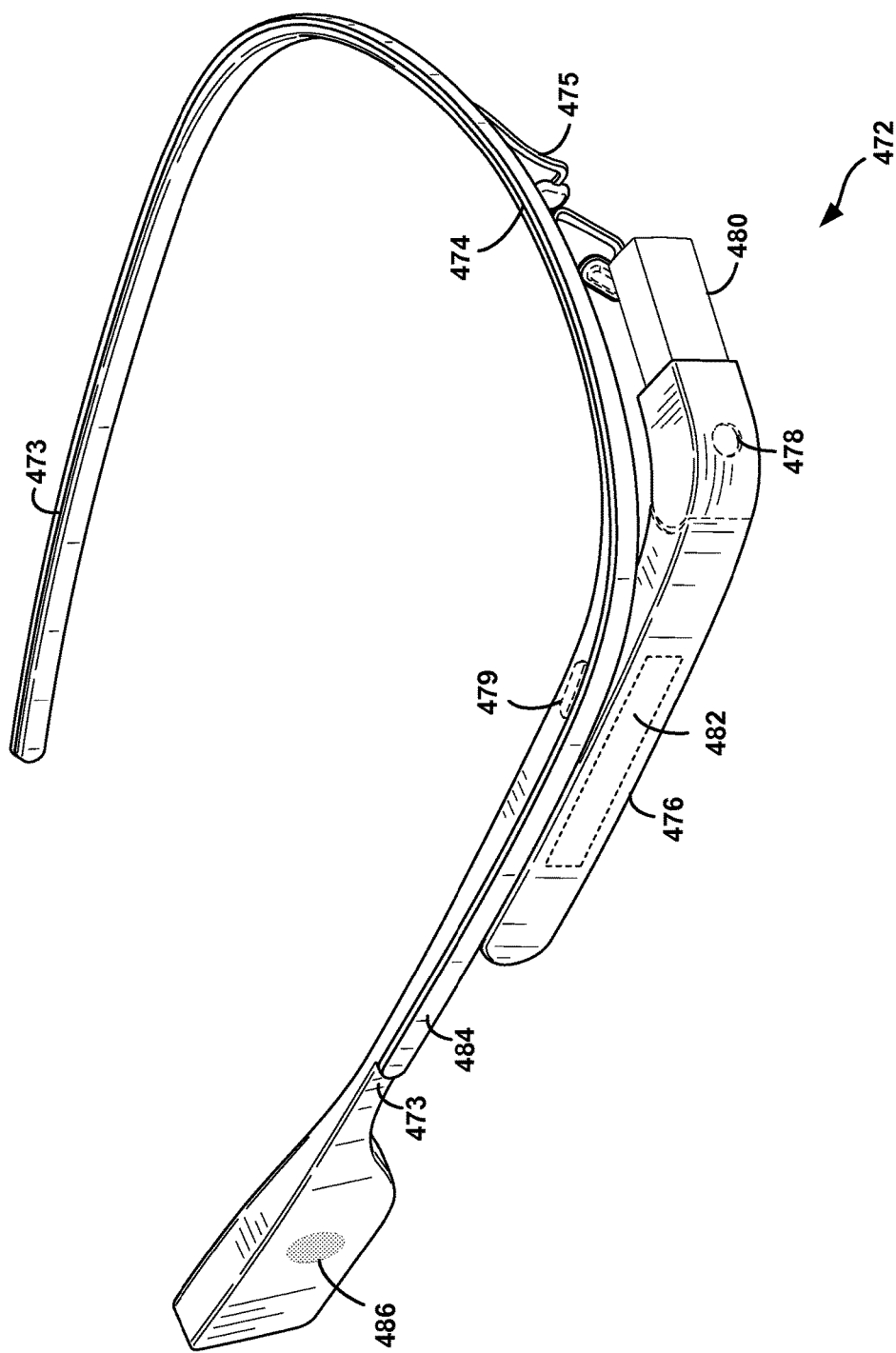
FIG. 4D illustrates another wearable computing system according to an example embodiment.

FIG. 4D illustrates another wearable computing system according to an example embodiment, which takes the form of a monocular HMD 472. The HMD 472 may include side-arms 473, a center frame support 474, and a bridge portion with nosepiece 475. In the example shown in FIG. 4D, the center frame support 474 connects the side-arms 473. The HMD 472 does not include lens-frames containing lens elements. The HMD 472 may additionally include a component housing 476, which may include an on-board computing system (not shown), an image capture device 478, and a button 479 for operating the image capture device 478 (and/or usable for other purposes). Component housing 476 may also include other electrical components and/or may be electrically connected to electrical components at other locations within or on the HMD. HMD 472 also includes a side-mounted touchpad 482 and a BCT 486.

The HMD 472 may include a single display 480, which may be coupled to one of the side-arms 473 via the component housing 476. In an example embodiment, the display 480 may be a see-through display, which is made of glass and/or another transparent or translucent material, such that the wearer can see their environment through the display 480. Further, the component housing 476 may include the light sources (not shown) for the display 480 and/or optical elements (not shown) to direct light from the light sources to the display 480. As such, display 480 may include optical features that direct light that is generated by such light sources towards the wearer's eye, when HMD 472 is being worn.

In a further aspect, HMD 472 may include a sliding feature 484, which may be used to adjust the length of the side-arms 473. Thus, sliding feature 484 may be used to adjust the fit of HMD 472. Further, an HMD may include other features that allow a wearer to adjust the fit of the HMD, without departing from the scope of the invention.

Figure 4E:
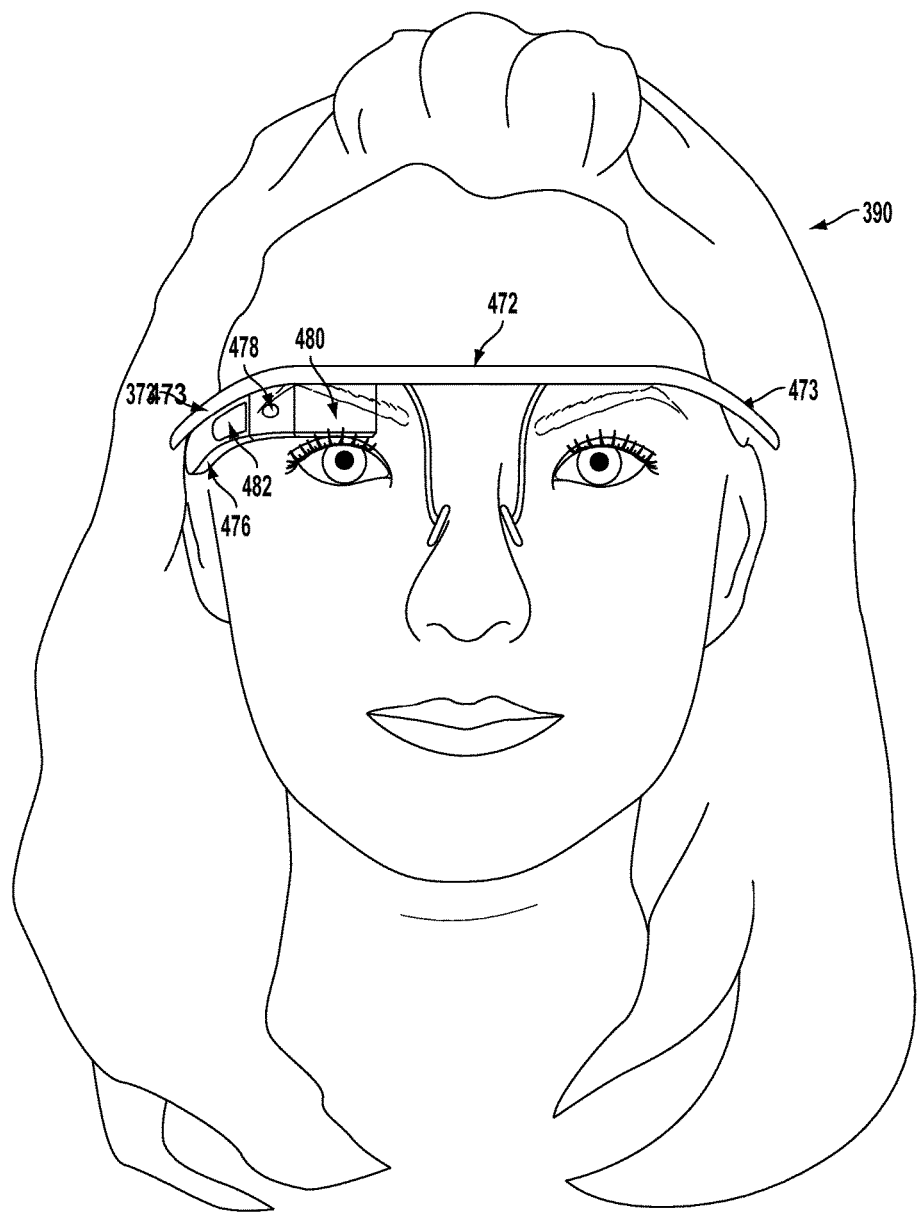
FIG. 4E to 4G are simplified illustrations of the wearable computing system shown in FIG. 4D, being worn by a wearer.
Figure 4F:
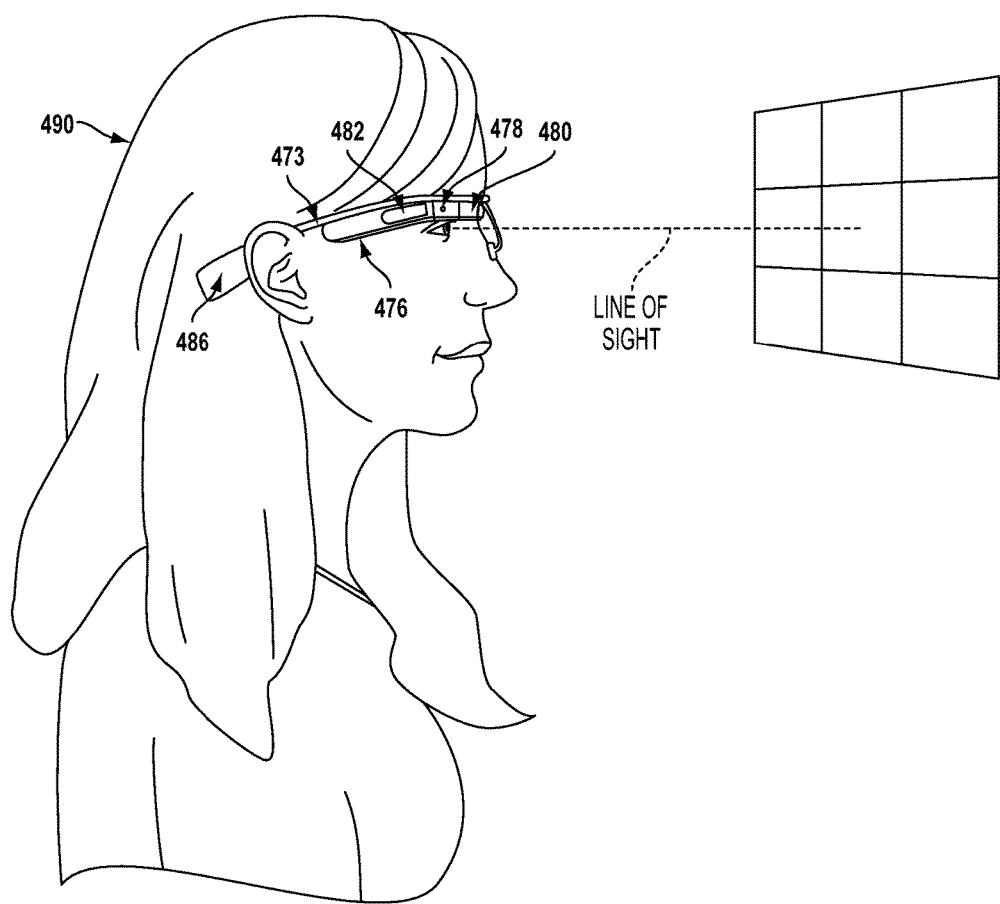
Figure 4G:
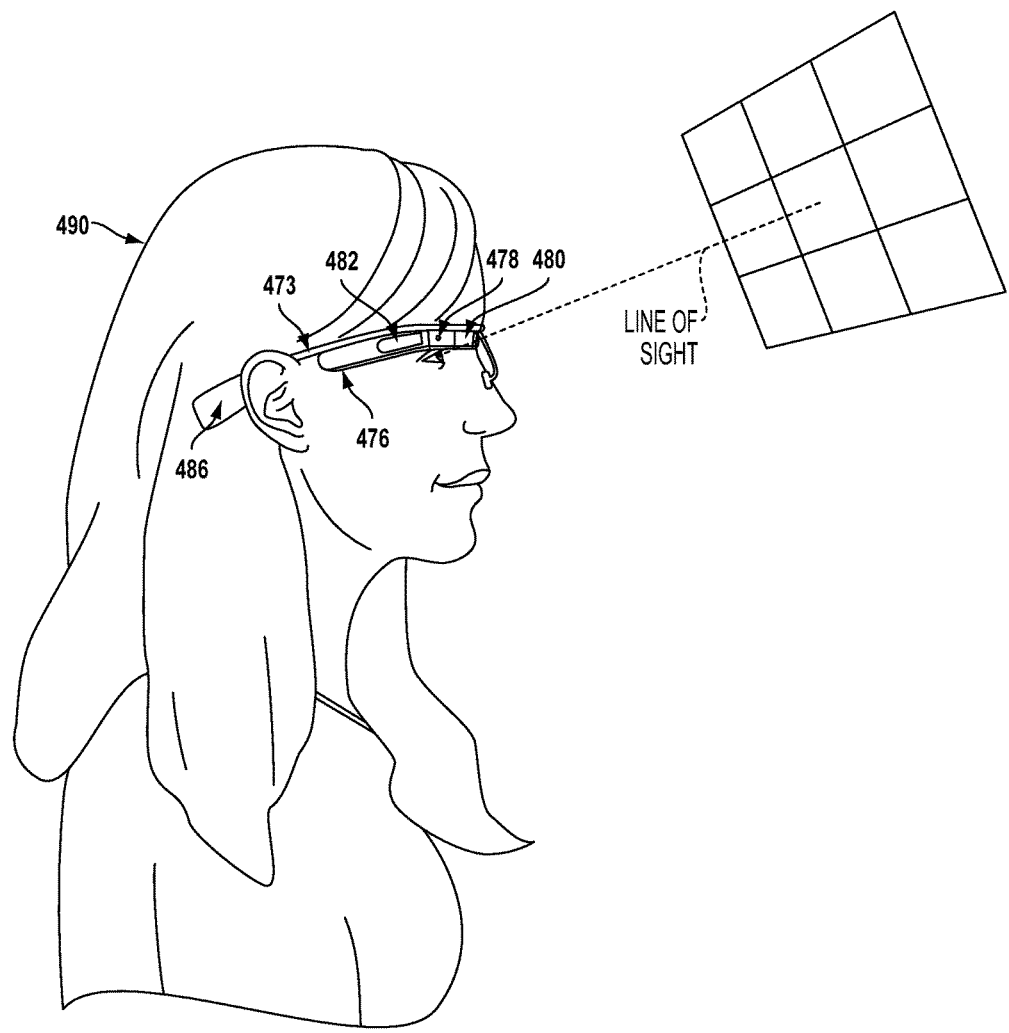

FIGS. 4E to 4G are simplified illustrations of the HMD 472 shown in FIG. 4D, being worn by a wearer 490. As shown in FIG. 4F, when HMD 472 is worn, BCT 486 is arranged such that when HMD 472 is worn, BCT 486 is located behind the wearer's ear. As such, BCT 486 is not visible from the perspective shown in FIG. 4E.

In the illustrated example, the display 480 may be arranged such that when HMD 472 is worn, display 480 is positioned in front of or proximate to a user's eye when the HMD 472 is worn by a user. For example, display 480 may be positioned below the center frame support and above the center of the wearer's eye, as shown in FIG. 4E. Further, in the illustrated configuration, display 480 may be offset from the center of the wearer's eye (e.g., so that the center of display 480 is positioned to the right and above of the center of the wearer's eye, from the wearer's perspective).

Configured as shown in FIGS. 4E to 4G, display 480 may be located in the periphery of the field of view of the wearer 490, when HMD 472 is worn. Thus, as shown by FIG. 4F, when the wearer 490 looks forward, the wearer 490 may see the display 480 with their peripheral vision. As a result, display 480 may be outside the central portion of the wearer's field of view when their eye is facing forward, as it commonly is for many day-to-day activities. Such positioning can facilitate unobstructed eye-to-eye conversations with others, as well as generally providing unobstructed viewing and perception of the world within the central portion of the wearer's field of view. Further, when the display 480 is located as shown, the wearer 490 may view the display 480 by, e.g., looking up with their eyes only (possibly without moving their head). This is illustrated as shown in FIG. 4G, where the wearer has moved their eyes to look up and align their line of sight with display 480. A wearer might also use the display by tilting their head down and aligning their eye with the display 480.

Figure 5:
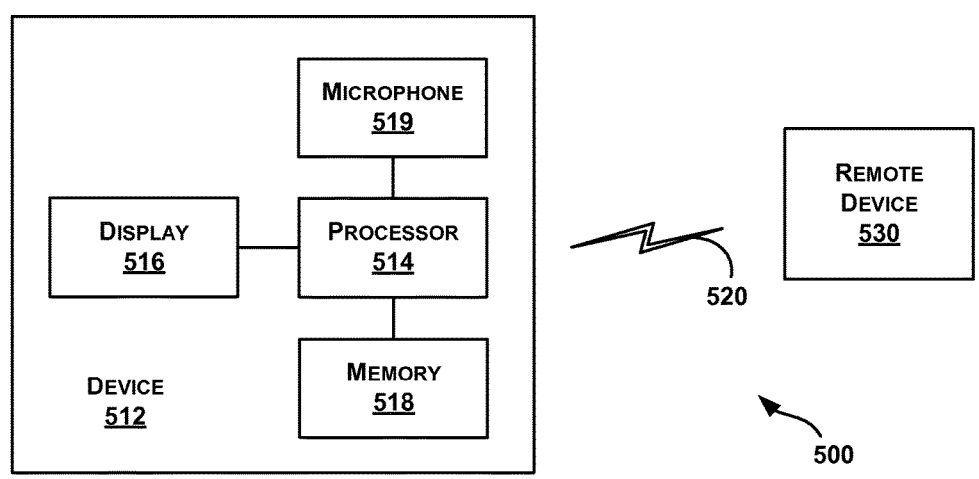
FIG. 5 is a simplified block diagram of a computing device according to an example embodiment.

FIG. 5 is a simplified block diagram of a system 500 including a computing device 510 according to an example embodiment. In an example embodiment, device 510 communicates using a communication link 520 (e.g., a wired or wireless connection) to a remote device 530. The device 510 may be any type of device that can receive data and display information corresponding to or associated with the data. For example, the device 510 may be a heads-up display system, such as the head-mounted devices 402, 452, or 472 described with reference to FIGS. 4A to 4G.

The device 510 may include a display system comprising a processor 514 and a display 516. The display 510 may be, for example, an optical see-through display, an optical see-around display, or a video see-through display. The processor 514 may receive data from the remote device 530, and configure the data for display on the display 516. The processor 514 may be any type of processor, such as a microprocessor or a digital signal processor, for example.

The device 510 may further include on-board data storage, such as memory 518, and a microphone 519, both coupled to the processor 514. The memory 518 may store software that can be accessed and executed by the processor 514, for example.

The remote device 530 may be any type of computing device or transmitter including a laptop computer, a mobile telephone, or tablet computing device, etc., that is configured to transmit data to the device 510. For example, the remote device 530 may be provided as the control system 130. The remote device 530 and the device 510 may contain hardware to enable the communication link 520, such as processors, transmitters, receivers, antennas, etc. Further, remote device 530 may take the form of or be implemented in a computing system that is in communication with and configured to perform functions on behalf of a client device, such as computing device 510. Such a remote device 530 may receive data from another computing device 510 (e.g., an HMD 402, 452, or 472 or a mobile phone), perform certain processing functions on behalf of the device 510, and then send the resulting data back to device 510. This functionality may be referred to as "cloud" computing.

In FIG. 2, the communication link 520 is illustrated as a wireless connection; however, wired connections may also be used. For example, the communication link 520 may be a wired serial bus such as a universal serial bus or a parallel bus. A wired connection may be a proprietary connection as well. The communication link 520 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. The remote device 530 may be accessible via the Internet and may include a computing cluster associated with a particular web service (e.g., social-networking, photo sharing, address book, etc.).

IV. EXAMPLE METHODS

Figure 6:
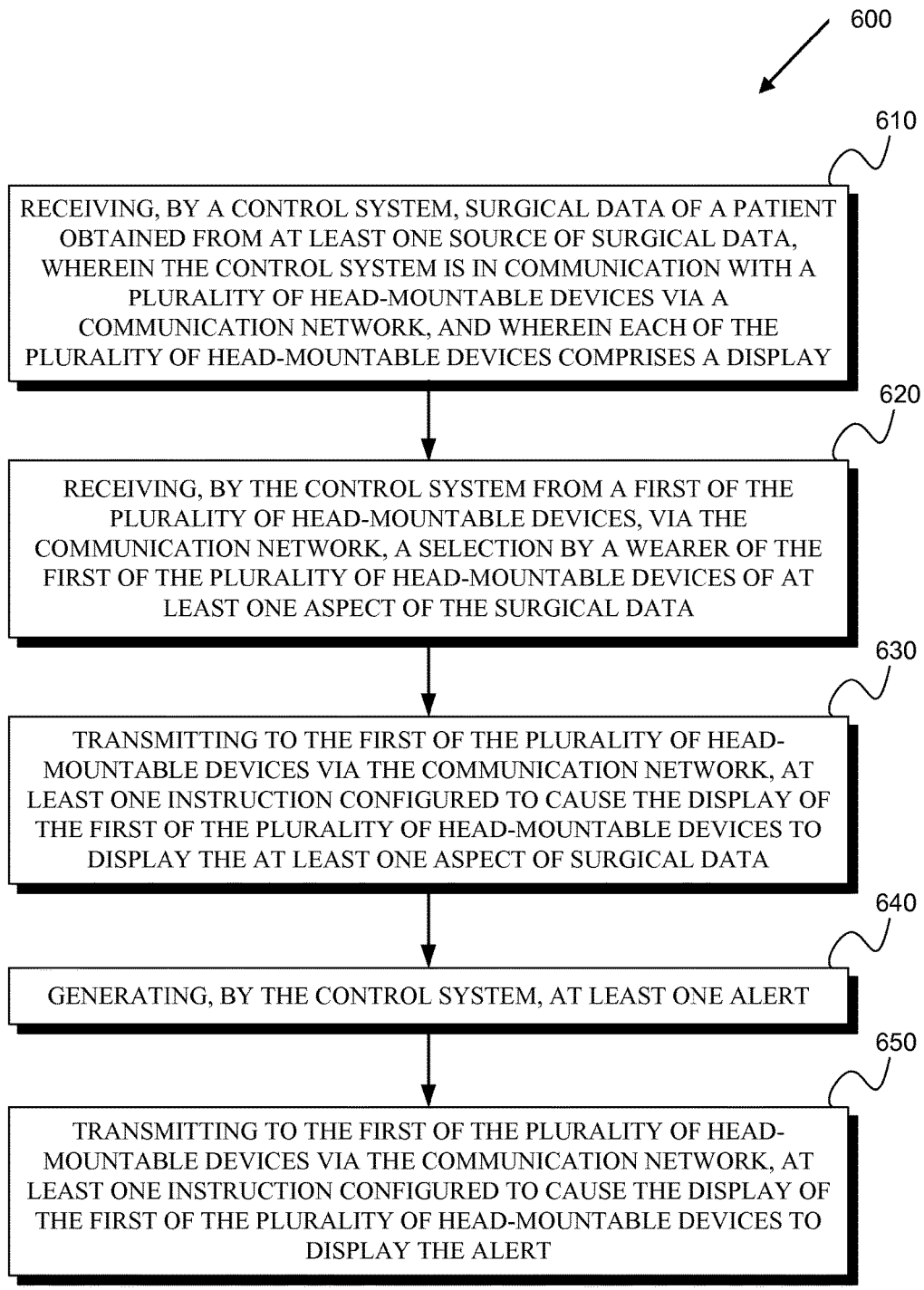
FIG. 6 is a flowchart of an example method.

FIG. 6 is a flowchart of an example method 600 for providing networked communications in a surgical setting. The method 600 may, for example, be carried out, at least in part, by any computing device, such as control system 130 described above. The control system receives surgical data of a patient obtained from at least one source of surgical data. (610). The control system is in communication with a plurality of HMDs, each comprising a display, via a communication network. The control system receives a selection by a wearer of at least one of the plurality of the HMDs of at least one aspect of the surgical data. (620). The surgical data and the sources of surgical data may be any of those described above, including surgical image data obtained from at least one image capture device and speech captured from at least one microphone. The control system transmits to the HMD from which the selection was made at least one instruction configured to cause the display of the first of that respective HMD to display the at least one aspect of surgical data. (630).

Figure 7:
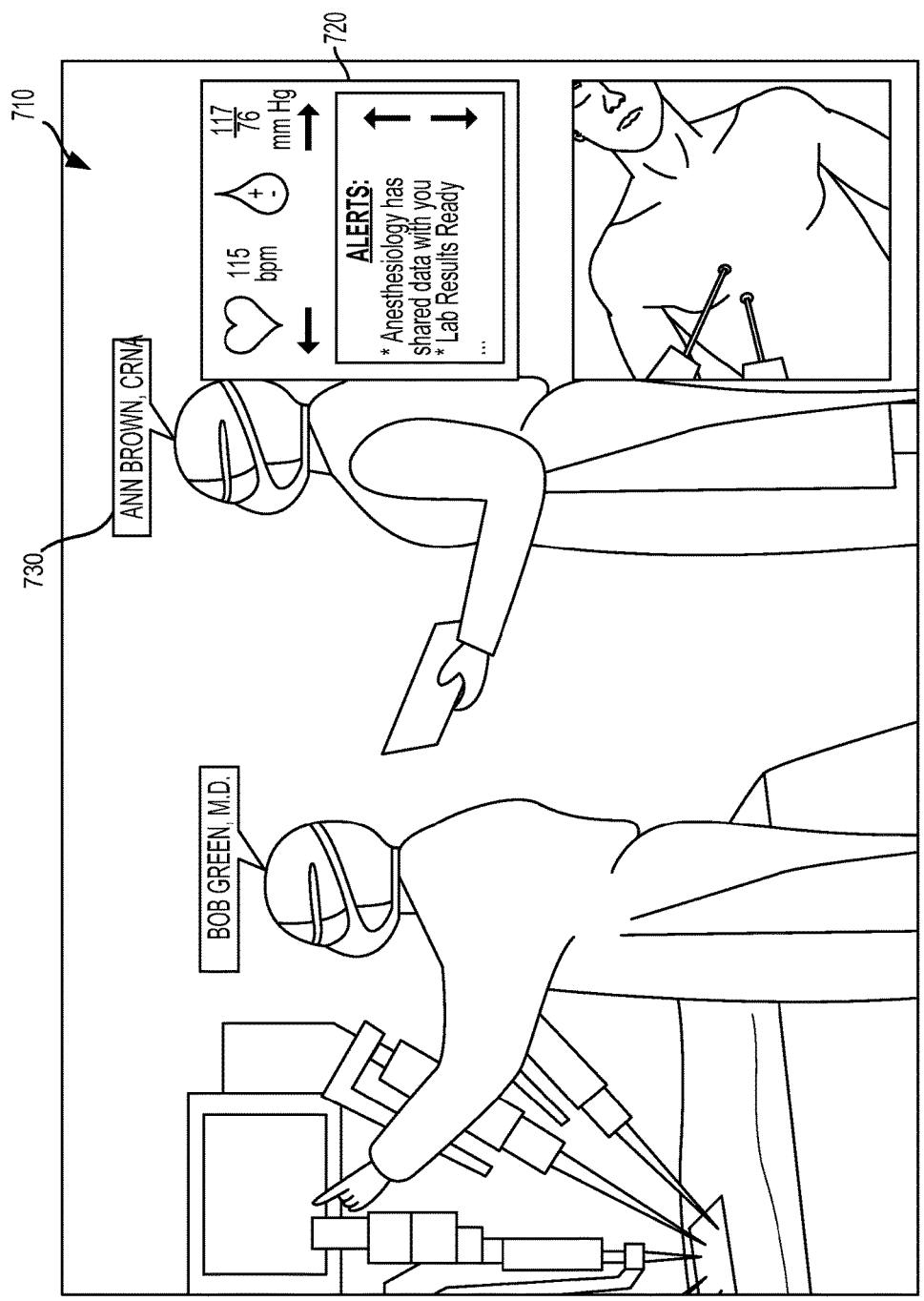
FIG. 7 illustrates an example user interface of a head-mountable device.

The control system is further configured to generate at least one alert (640) and transmit to at least one of the HMDs instruction configured to cause the display of the first of the plurality of head-mountable devices to display the alert (650). As described above, the alert may be a notification that additional surgical data is available for access by at least one of the HMDs. The control system may instruct the display of the HMD to display the alert in any manner perceivable by the wearer of the HMD. As shown in FIG. 7, the alert may, as described above, be presented in a navigation pane 720 projected on the display 710. In some cases, the alert may flash or vibrate to obtain the attention of the wearer of the HMD. In other examples, the control system may additionally or alternatively instruct the HMD to provide some other indication of an alert, such as a tactile or auditory indication. In addition, the alert may, as shown in FIG. 7, comprise the name of a wearer of an HMD that is within the field of view of the wearer of an HMD. The alert may be presented on the display 710 in the form of a callout 730 positioned above the head of one or more other members of the surgical team that the wearer sees within her field of view.

In further examples, the control system may transmit, via the communication network, to each of the plurality of HMDs, at least one instruction configured to cause the respective display of each of the plurality of head-mountable devices to display an action item, which may include any event, task, step, activity, or action that needs to take place in a surgical scenario or procedure. The action item may, in some cases, include all or part of a checklist. The action item transmitted to and displayed on a respective display may include one or more items or steps and may include all or part of a larger list of items. For example, as some surgical action items may include many events or steps, the action item displayed on the HMD may be only a portion of the entire set of items on the list, such as items that are relevant to the part of the surgery currently being performed. Such an action item may be a specific action, such as a cut or a suture placement, or a piece of information to be checked, for example which of the left or right limb is the correct one for needed surgery. As an action item is completed by one or more surgical team members or as a surgical procedure progresses to different stages, the HMD display may scroll or update to the next item on the list. In some examples, the HMD may be configured to display the name of an action item and "preview" the next step to be performed.

Also, in some examples, the HMD displays of different team members may display different action items. The action item displayed on a particular HMD might be customized to the roles or tasks assigned to that team member. The HMD may also be configured to indicate the roles of each team member by, for example, highlighting the team member (e.g., with a flashing light) responsible for a particular action item. The action item may be generated by the control system, or may be generated by a remote computing device and transmitted to the control system.

Responses to action items generated by individual wearers of the plurality of HMDs are received by the control system via the communication network. Wearers may generate responses based on commands recognized by their respective HMDs, including verbal commands, gestures and eye movements. Upon receiving responses, the control system transmits, via the communication network, at least one instruction configured to cause the display of at least one of the plurality of head-mountable devices to display a received response to an action item. In some examples, the control system may cause the received responses to be displayed on each of the plurality of HMDs, or only a subset thereof. Accordingly, one or more wearers of an HMD may become visually aware of the responses to action items generated by other surgical team members, thereby facilitating communication between members of the team. Discrepancies in action item responses, or unexpected responses, may be brought to the attention of and be addressed by one or more members of the surgical team.

In some examples, the control system may further transform at least one aspect of the surgical data of the patient, obtained from at least one source of surgical data, to generate transformed surgical data. Generating transformed surgical data can include generating a layered surgical image, as will be described in more detail below. Other transformations of the surgical data by the control system are also contemplated. For example, the control system may rotate or translate the surgical image data to create additional or modified views of the surgical field, or to create perspective views from the point of view of one or more of the surgical team members based on the member's position relative to the patient's body. The control system may also transform the surgical data by, for example, adding color to certain aspects of surgical video data to highlight a particular anatomical structure or a surgical instrument.

The control system is further configured to transmit to an HMD at least one instruction configured to cause the display of the respective HMD to display the transformed surgical data, such as a layered surgical image. A layered surgical image may comprise an additional aspect of the surgical data superimposed on, for example, surgical video data, where the wearer of an HMD initially selected that surgical image data be displayed on her respective HMD. In some examples, the additional aspect of the surgical data comprises one or more of fluorescent image data, spectral image data, and hyperspectral image data. Accordingly, the layered image may include fluorescent image data overlaid on surgical video data being projected on the display of the wearer's HMD. The additional surgical data may also comprise images of an anatomical structure of the patient. For example, the control system may generate a layered image comprising an image of a key structure such as the ureter superimposed over video images gathered from, for example, an endoscope. This feature may allow the entire surgical team to ensure that the instruments are nowhere near the key structure or pay extra attention when they are. The anatomical structure images may be pre-operative images, images captured from one or more of the surgical instruments or image capture devices located within the operating room, or they may be computer-generated images.

The additional aspect of the surgical data used to generate a layered surgical image may also include a computer graphics model of at least one surgical instrument. In some examples, it may be desirable for members of a surgical team other than the surgeon to view the surgical instruments and how the surgical instruments are moving within the surgical field. However, in practice, a view of the surgical instruments may be occluded from certain perspectives or positions within the operating room even when rotated or translated as described above. Accordingly, a computer graphics model of the surgical instruments may be rendered and superimposed over the surgical video. In some examples, the computer graphics model of a surgical instrument may be rendered by a remote computing device. In general, because the surgical instruments are engineered products, the specifications and information necessary to generate such models will be known. Further, in the case of robotic instruments, the movement and positions of the instruments and tools can be determined based on feedback from position sensors on the instruments and also, to some extent, based on commands given to the instruments by the surgeon. For non-robotic instruments and tools, tracking systems and devices (such as a surgical navigation system) may be used to provide position and movement information necessary to generate the computer graphics model. Image data gathered from an endoscope and the known position and orientation of the endoscope can also be used to determine the position and orientation of other instruments and tools, both robotic and manual.

Figure 8:
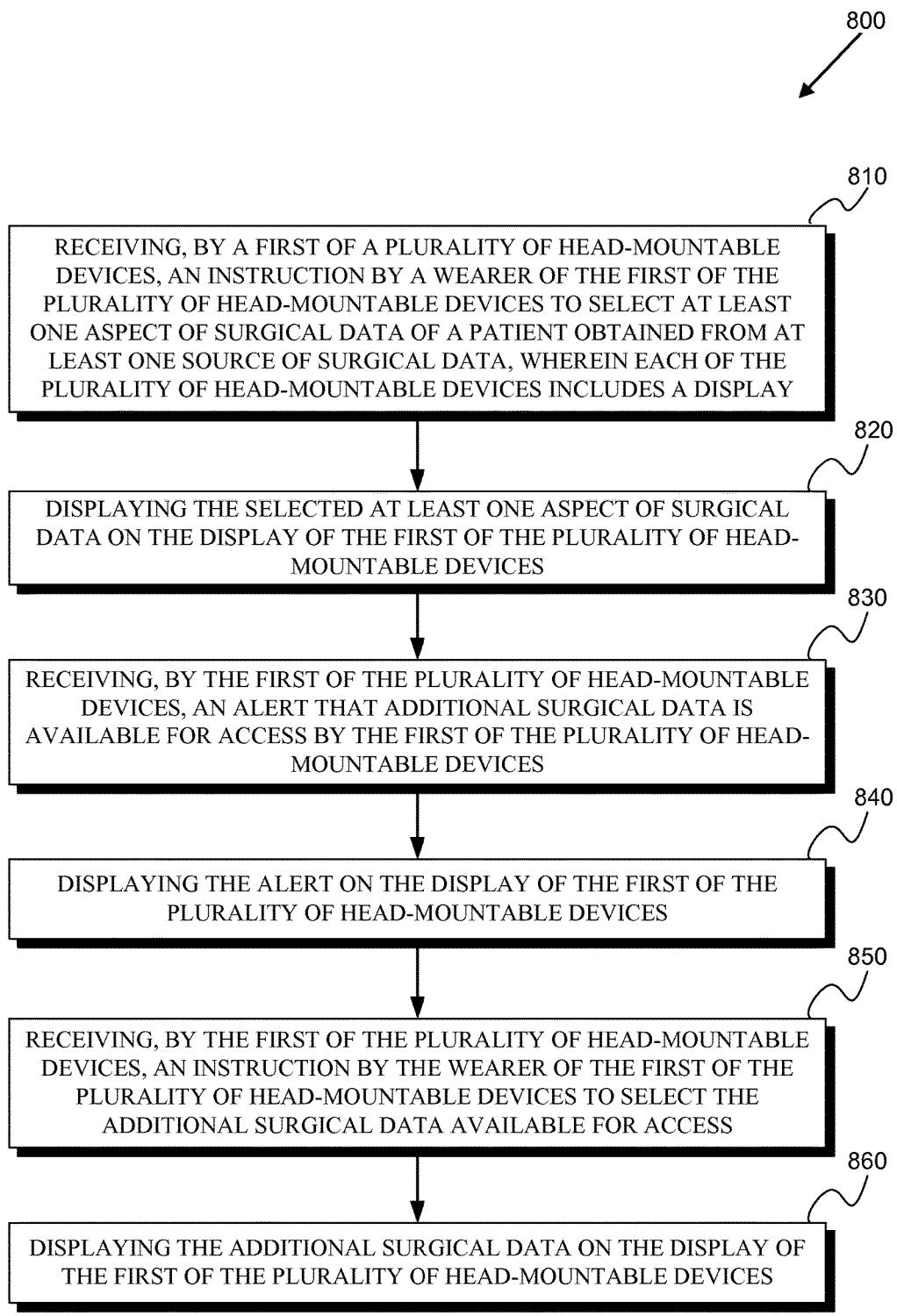
FIG. 8 is a flowchart of an example method.

FIG. 8 is a flowchart of an example method 800 for providing networked communications in a surgical setting among a plurality of HMDs. The method 600 may, for example, be carried out, at least in part, by any computing device, such as control system 130 or any wearable computing device, such as HMD 112, described above. A wearer of one of a plurality of HMDs selects at least one aspect of surgical data of a patient obtained from at least one source of surgical data. The respective HMD receives the wearer's instruction to select the aspect of surgical data (810) and displays the selected surgical data on the display of the respective HMD (820). Further, the HMD receives an alert from, for example, control system 130 or another HMD 112 that additional surgical data is available for access (830) and displays the alert on the display of the respective HMD (840). The alert may be any of the alerts described above and may be presented on the display in any of the manners described above. The wearer of the HMD may instruct the HMD to select the additional surgical data (850) by any command recognized by the HMD, such as the verbal, eye movement or gesture commands described above. The additional surgical data is displayed on the display of the respective HMD. (860). In some examples, a checklist may also be displayed on the respective display of each of the plurality of HMDs and responses to checklist items received by at least one of the plurality of HMDs may also be displayed on the respective display of each of the plurality of head-mountable devices.

V. CONCLUSION

While various aspects and embodiments have been disclosed herein, other aspects and embodiments will be apparent to those skilled in the art. The various aspects and embodiments disclosed herein are included for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein. The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

Further, in situations in where embodiments discussed herein collect personal information about users, or may make use of personal information, the users may be provided with an opportunity to control whether programs or features collect user information (e.g., information about a user's medical history, information about a surgical intervention performed on the user, information about biological tissues of a user, a user's preferences, or a user's current location), or to control whether and/or how to receive content from a content server (e.g., a profile of power to ablate a tissue applied using a heating laser) that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a hospital, city, ZIP code, or state level), so that a particular location of a user cannot be determined. Thus, the user may have control over how information is collected about the user and used by a content server.

What is claimed is:

1. A method comprising:
    receiving, by a control system, surgical data of a patient obtained from at least one source of surgical data, wherein the control system is in communication with a plurality of head-mountable devices via a communication network, and wherein each of the plurality of head-mountable devices comprises a display;
    receiving, by the control system from a first of the plurality of head-mountable devices, via the communication network, a selection by a wearer of the first of the plurality of head-mountable devices of at least one aspect of the surgical data;
    transmitting to the first of the plurality of head-mountable devices via the communication network, at least one instruction configured to cause the display of the first of the plurality of head-mountable devices to display the at least one aspect of surgical data;
    generating, by the control system, at least one alert, wherein the at least one alert comprises a notification that a wearer of a second of the plurality of head-mountable devices has made additional surgical data available for access by the first of the plurality of head-mountable devices; and
    transmitting to the first of the plurality of head-mountable devices via the communication network, at least one instruction configured to cause the display of the first of the plurality of head-mountable devices to display the at least one alert.

2. The method of claim 1, wherein the at least one alert further comprises the name of the wearer of the second one of the plurality of head-mountable displays.

3. The method of claim 1, wherein the at least one alert further comprises a notification that additional surgical data is available for access by the at least one of the plurality of head-mountable devices.

4. The method of claim 1, further comprising:
    receiving, by the control system from first of the plurality of head-mountable devices via the communication network, an instruction to make additional surgical data available for access by the second of the plurality of head-mountable devices.

5. The method of claim 1, wherein the at least one alert further comprises a notification that one of the at least one sources of surgical data has made additional surgical data available for access by the first of the plurality of head-mountable devices.

6. The method of claim 1, wherein the surgical data comprises surgical image data captured by a camera provided on at least one of the plurality of head-mountable devices.

7. The method of claim 1, wherein the surgical data comprises speech captured by a microphone provided on at least one of the plurality of head-mountable devices.

8. The method of claim 1, wherein the surgical data comprises pre-surgical images of a patient.

9. The method of claim 1, wherein the surgical data comprises surgical parameter data collected from at least one surgical instrument.

10. The method of claim 1, wherein the surgical data comprises patient data collected from at least one source of patient data.

11. The method of claim 1, further comprising:
transmitting to at least one of the plurality of head-mountable devices via the communication network, at least one instruction configured to cause the respective display of the at least one of the plurality of head-mountable devices to display an action item;
receiving, by the control system from at least one of the plurality of head-mountable devices, via the communication network, a response to the action item; and
transmitting to at least one of the plurality of head-mountable devices via the communication network, at least one instruction configured to cause the respective display of the at least one of the plurality of head-mountable devices to display the response to the at least one action item.

12. The method of claim 11, wherein the action item is a checklist.

13. The method of claim 1, further comprising:
transforming, by the control system, at least one aspect of the surgical data of a patient obtained from at least one source of surgical data to generate transformed surgical data; and
transmitting to the first of the plurality of head-mountable devices via the communication network, at least one instruction configured to cause the display of the first of the plurality of head-mountable devices to display the transformed surgical data.

14. The method of claim 13, wherein the at least one aspect of the surgical data comprises surgical video data of a patient, and further wherein transforming, by the control system, at least one aspect of the surgical data of a patient obtained from at least one source of surgical data to generate transformed surgical data comprises:
generating a layered surgical image comprising an additional aspect of the surgical data superimposed on the surgical video data.

15. The method of claim 14, wherein the additional aspect of the surgical data comprises one or more of fluorescent image data, spectral image data, and hyperspectral image data.

16. The method of claim 14, wherein the additional aspect of the surgical data comprises a computer graphics model of at least one surgical instrument.

17. The method of claim 14, wherein the additional aspect of the surgical data comprises an image of at least one anatomical structure of a patient.

18. A method comprising:
receiving, by a first of a plurality of head-mountable devices, an instruction by a wearer of the first of the plurality of head-mountable devices to select at least one aspect of surgical data of a patient obtained from at least one source of surgical data, wherein each of the plurality of head-mountable devices includes a display;
displaying the selected at least one aspect of surgical data on the display of the first of the plurality of head-mountable devices;
receiving, by the first of the plurality of head-mountable devices, an alert that additional surgical data is available for access by the first of the plurality of head-mountable devices, wherein the alert comprises a notification that a wearer of a second of the plurality of head-mountable devices has made the additional surgical data available for access by the first of the plurality of head-mountable devices; and
displaying the alert on the display of the first of the plurality of head-mountable devices.

19. The method of claim 18, further comprising:
receiving, by the first of the plurality of head-mountable devices, an instruction by the wearer of the first of the plurality of head-mountable devices to select the additional surgical data available for access; and
displaying the additional surgical data on the display of the first of the plurality of head-mountable devices.

20. The method of claim 18, wherein the surgical data comprises surgical image data captured by a camera provided on at least one of the plurality of head-mountable devices.

21. The method of claim 18, wherein the alert further comprises a notification that one of the at least one sources of surgical data has made additional surgical data available for access by the first of the plurality of head-mountable devices.

22. The method of claim 18, further comprising:
receiving, by the first of the plurality of head-mountable devices, an instruction by the wearer of the first of the plurality of head-mountable devices to make additional surgical data available for access by the second of the plurality of head-mountable devices.

23. The method of claim 18, further comprising:
displaying a checklist on the respective display of each of the plurality of head-mountable devices;
receiving, by at least one of the plurality of head-mountable devices, a response to at least one checklist item; and
displaying the response to the at least one checklist item on the respective display of each of the plurality of head-mountable devices.

24. A system comprising:
a plurality of head-mountable devices, each of the plurality of head-mountable devices comprising a display; and
a control system in communication with each of the plurality of head-mountable devices via a communication network, the control system comprising:
a processor;
a computer-readable medium; and
program instructions stored in the computer readable medium, wherein the program instructions are executable by the processor to cause the control system to perform functions comprising:
receiving, via the communication network, surgical data of a patient obtained from at least one source of surgical data;
receiving from a first of the plurality of head-mountable devices, via the communication network, a selection of at least one aspect of the surgical data made by a wearer of the first of the plurality of head-mountable devices;
transmitting to the first of the plurality of head-mountable devices via the communication network, at least one instruction configured to cause the display of the first of the plurality of head-mountable devices to display the at least one aspect of surgical data;

generating at least one alert, wherein the at least one alert comprises a notification that a wearer of a second of the plurality of head-mountable devices has made additional surgical data available for access by the first of the plurality of head-mountable devices; and transmitting to the first of the plurality of head-mountable devices via the communication network, at least one instruction configured to cause the display of the first of the plurality of head-mountable devices to display the at least one alert.

25. The system of claim 24, wherein at least one of the plurality of head-mountable devices comprises an image capture device and wherein the surgical data comprises surgical image data obtained by the image capture device.

26. The system of claim 24, wherein at least one of the plurality of head-mountable devices comprises a microphone and wherein the surgical data comprises speech captured by the microphone.

27. The system of claim 24, wherein the at least one alert further comprises the name of the wearer of the second one of the plurality of head-mountable displays that is within the field of view of the wearer of the first of the plurality of head-mountable devices.

* * * * *